(12) United States Patent
Al-Salem

(10) Patent No.: US 6,672,309 B1
(45) Date of Patent: Jan. 6, 2004

(54) CONDOM

(76) Inventor: Sami Al-Salem, P.O. Box 125, Postal Code 13002, Safat (KW)

( * ) Notice: Subject to any disclaimer, the term of this patent is extended or adjusted under 35 U.S.C. 154(b) by 23 days.

(21) Appl. No.: 10/183,428

(22) Filed: Jun. 28, 2002

(51) Int. Cl.[7] .................................................. A61F 6/04
(52) U.S. Cl. ...................................... 128/844; 128/918
(58) Field of Search ................................ 128/842, 844, 128/918; 604/347–353

(56) References Cited

U.S. PATENT DOCUMENTS

| | | | | |
|---|---|---|---|---|
| 2,586,674 A | * | 2/1952 | Loane ........................ 128/844 |
| 3,809,090 A | * | 5/1974 | Povlacs ...................... 128/294 |
| 4,852,586 A | * | 8/1989 | Haines ........................ 128/842 |
| 4,881,553 A | * | 11/1989 | Grossman ................... 604/347 |

* cited by examiner

Primary Examiner—Michael A. Brown
(74) Attorney, Agent, or Firm—Dennison, Schultz & Dougherty

(57) ABSTRACT

A condom includes a flexible tubular body having an open and a closed end, an outer surface and a smooth inner surface. The tubular body is formed of thin homogenous elastomeric material having a generally constant diameter from its open to its closed end to define a longitudinally extending chamber. The tubular body also includes a plurality of outwardly extending flexible lash-like projections extending from the outer surface of the tubular body and fixed to a tubular body along one side thereof.

7 Claims, 3 Drawing Sheets

CONDOM

FIELD OF INVENTION

This invention relates to an improved condom and more particularly to a condom for providing enhanced stimulation.

BACKGROUND FOR THE INVENTION

The importance of using condoms particularly in casual sexual activities is well known. Nevertheless, many sexual partners are reluctant to use such devices to avoid pregnancy and the risk of sexually transmitted diseases. Often, the reluctance to use condoms is based on the loss of tactile sensation during copulation.

Accordingly, it is desirable to have a device which in addition to being impervious to the passage of either pathogens or sperm will not cause the loss of tactile sensations and generally enhance the sensory perception of the user. One approach for providing an improved device is disclosed in the Haines U.S. Pat. No. 4,852,586 entitled sensory transmitting membrane device. That reference is incorporated herein in its entirety by reference.

It is also well known that in sexual relationships, the responsiveness of a female may vary to a great extent from the responsiveness of a male. In such cases, the male tends to reach the climax of sexual intercourse before the female. This disparity and lack of unity in obtaining climax is considered to be a significant and often basic factor leading to incompatibility and general matrimonial difficulties. One approach to overcome such problems is disclosed in the Freeman U.S. Pat. No. 2,816,542 which is also incorporated herein in its entirety by reference. As disclosed in the Freeman patent, a prophylactic tube incorporates means for inhibiting the degree of stimulation of the critical area of sensitivity of the male organ, while at the same time providing the general sensation of intercourse in other areas.

It is now believed that there may be a significant demand for an improved condom which provides enhanced stimulation and at the same time overcomes the problem associated with prior art devices. It is also believed that the improved condoms of the present invention will provide the same protection against unwanted pregnancy and sexually transmitted diseases, can be made of the same material as prior art devices and manufactured at a competitive cost.

BRIEF SUMMARY OF THE INVENTION

In essence, the present invention contemplates an improved condom which includes means for enhanced stimulation. The condom comprises a flexible tubular body having an open end, a closed end, an outer surface and a smooth inner surface. The tubular body is formed of a thin homogeneous elastomeric membrane having a generally constant diameter from its open to its closed end to thereby define a longitudinally extending chamber. The thin homogenous elastomeric membrane may be made of latex, or other material of the type used in conventional condoms. However, the condom in accordance with the present invention also includes a plurality of outwardly extending flexible lash-like projections extending from the outer surface of the tubular body and fixed to the tubular body along one side thereof. In a preferred embodiment of the invention, the outwardly extending projections have a length to width ratio of between about 5:1 and about 9:1 and are disposed between 4 and 5 longitudinally extending rows of 8 to 9 projections.

The invention will now be described in connection with the accompanying figures wherein like reference numerals have been used to indicate like parts.

DETAILED DESCRIPTION OF THE PREFERRED EMBODIMENTS OF THE INVENTION

Figure 1:
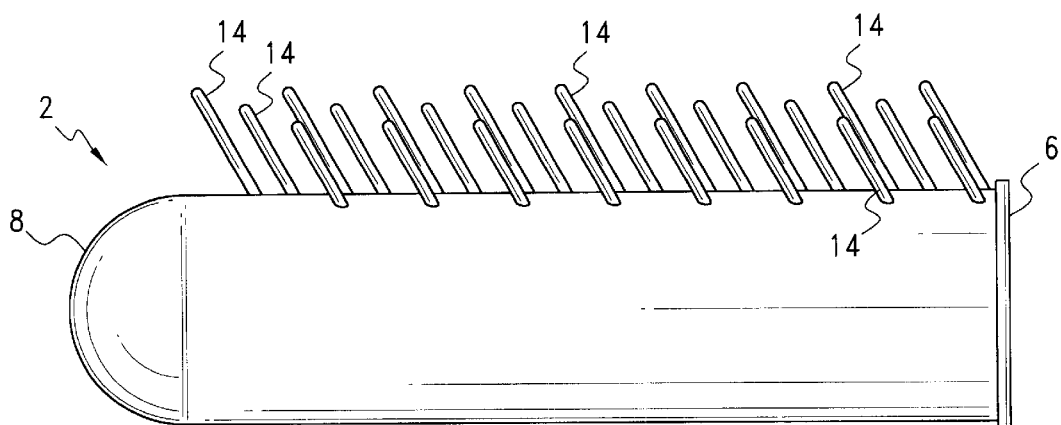
FIG. 1 is a side view of an improved condom in accordance with a first embodiment of the invention.
Figure 2:
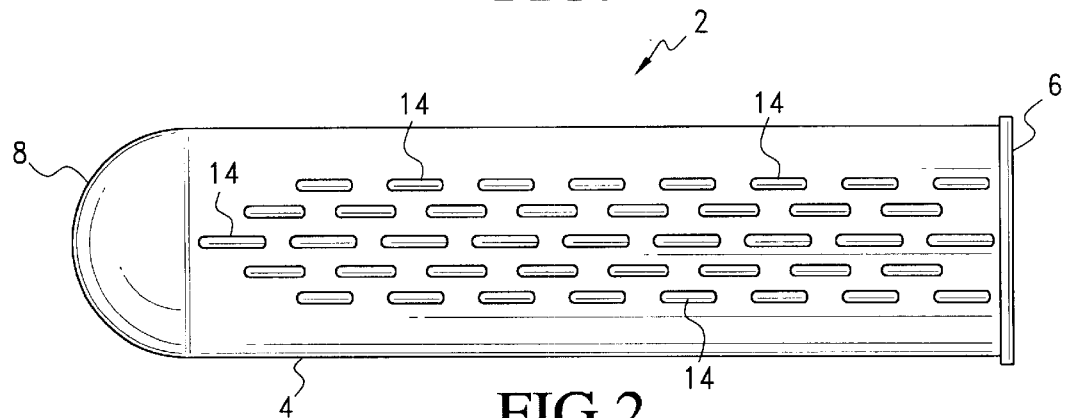
FIG. 2 is a top view of the condom shown in FIG. 1.
Figure 3:
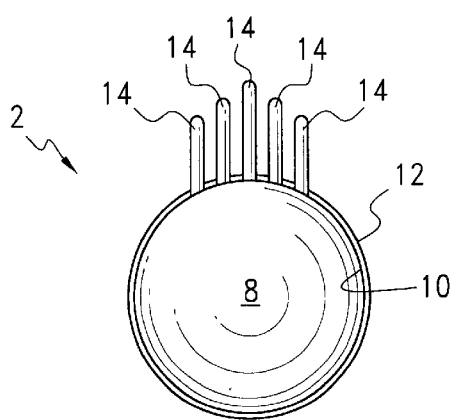
FIG. 3 is a front view of the condom shown in FIGS. 1 and 2.
Figure 4:
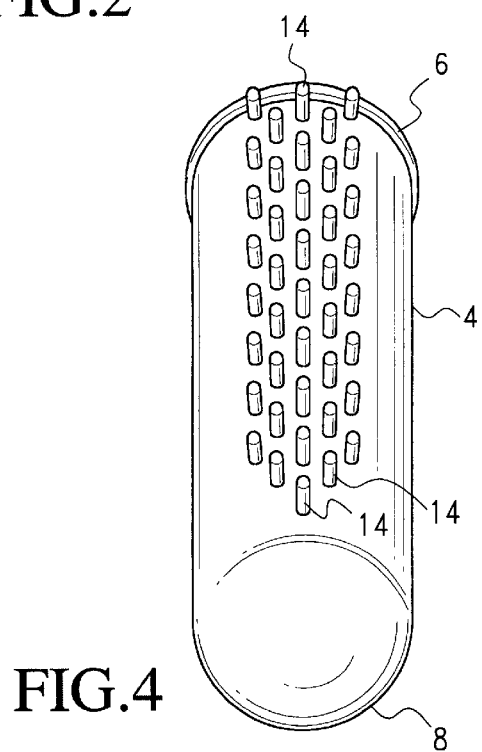
FIG. 4 is a schematic illustration showing a front-top view of a condom shown in FIGS. 1–3.

An improved condom in accordance with a first embodiment of the invention is illustrated in FIGS. 1–4. As illustrated therein, a condom 2 comprises a flexible tubular body 4 having an open end 6 and a closed end 8. The tubular body 4 with its open end 6 and closed end 8 is generally similar to a conventional condom and made of the same materials as commonly used in the industry. The tubular body 4 also includes a smooth inner surface 10 (FIG. 3) in the same manner as a conventional device and an outer surface 12 (FIG. 3).

In the first embodiment of the invention, the tubular body 41 includes a plurality of flexible outwardly extending lash-like projections 14. In the first embodiment of the invention, the lash-like projections 14 have a generally uniform length of between about 10 mm and about 18 mm, preferably about 10 mm, a thickness of about 2 mm and about a 12 mm spacing between projections. The projections also extend along one side of the tubular body 4 to within about 25 mm from the closed end 8.

The lash-like projections 14 may be made of a similar composition as the tubular body or may be compounded to reduce their flexibility or slightly increase their stiffness as will be well understood by a person of ordinary skill in the art. The lash-like projections may also be molded integrally with the tubular body 4 or otherwise permanently affixed thereto in a manner as will be well understood by persons of ordinary skill in the art. In general, the lash-like projections are thicker than the thin membranes.

As set forth above, the tubular body 4 is formed of a thin homogenous elastomeric material such as latex or other materials. In other words, the tubular body 4 is formed of a unitary prophylactically impermeable elastomeric material as for example, latex or rubber which is highly flexible and elastic and may be manufactured using any of the well known molding processes. For example, the condom may be formed by injection molding with the lashes inserted into the mold prior to injection of a plastic material.

Figure 5:
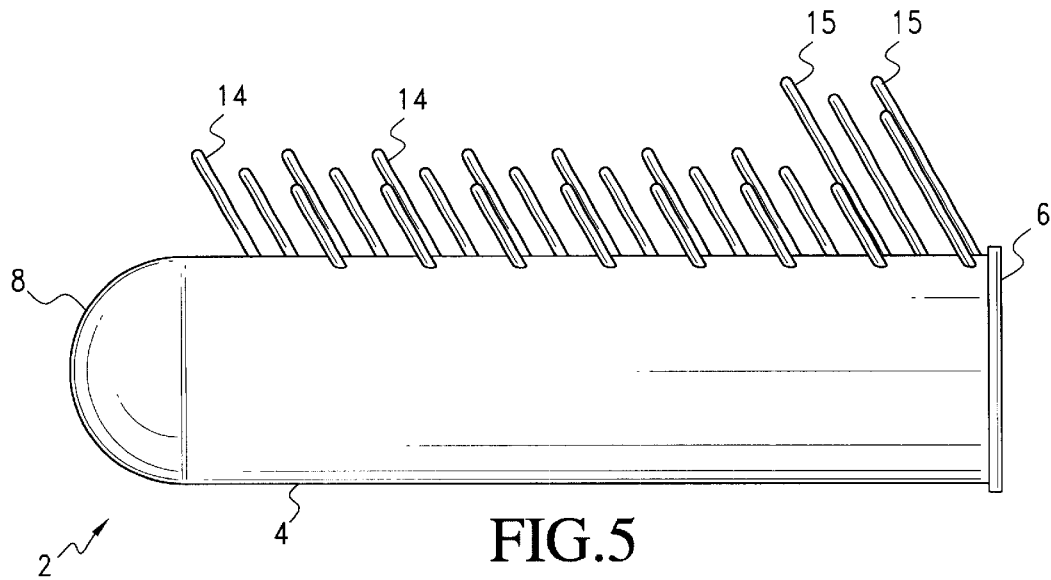
FIG. 5 is a side view of a condom according to a second embodiment of the invention.

The second embodiment of the invention is illustrated in FIG. 5 and is generally similar to the first embodiment of the invention. However, the second embodiment of the invention includes lash-like projections 14 and 15 wherein the projections 14 in a forward portion of the tubular body are of a first uniform height as for example approximately 10 mm in length while a second number of lash-like projections 15 have a length of about 18 mm and are located nearer to the open end 6 of the tubular body 4. As in the first and other embodiments of the invention, the lash-like projections extend outwardly from one side, i.e. the top side of the tubular body 4.

Figure 6:
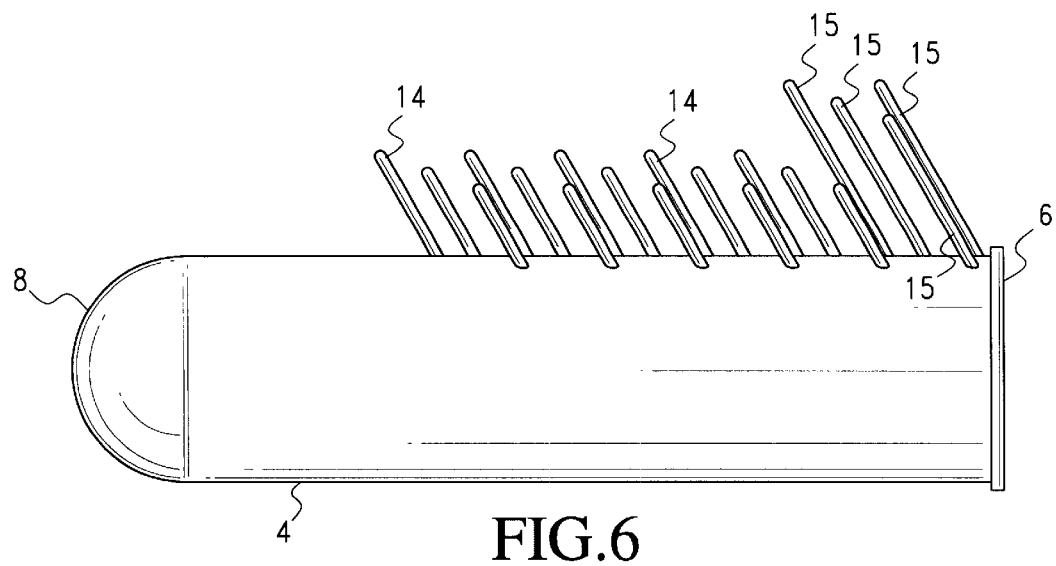
FIG. 6 is a side view of a condom according to a third embodiment of the invention.

FIG. 6 illustrates a third embodiment of the invention. As illustrated therein, the third embodiment of the invention is generally similar to the second embodiment of the invention. However, in the third embodiment of the invention, the projections 14 and 15 extend over about ⅔ of the length of the tubular body so that a forward portion of the tubular body is free of projections along about 25 to 33% of its length.

Figure 7:
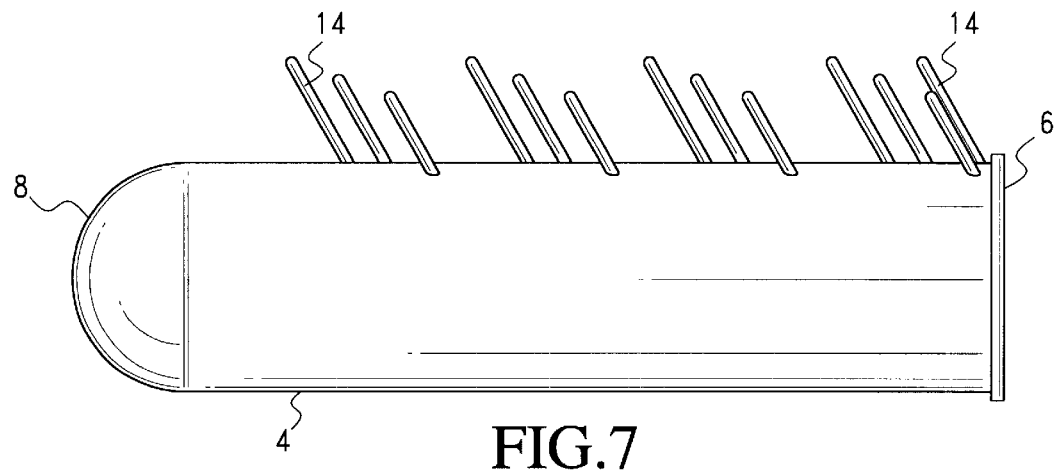
FIG. 7 is a side view of the condom according to a fourth embodiment of the invention.
Figure 8:
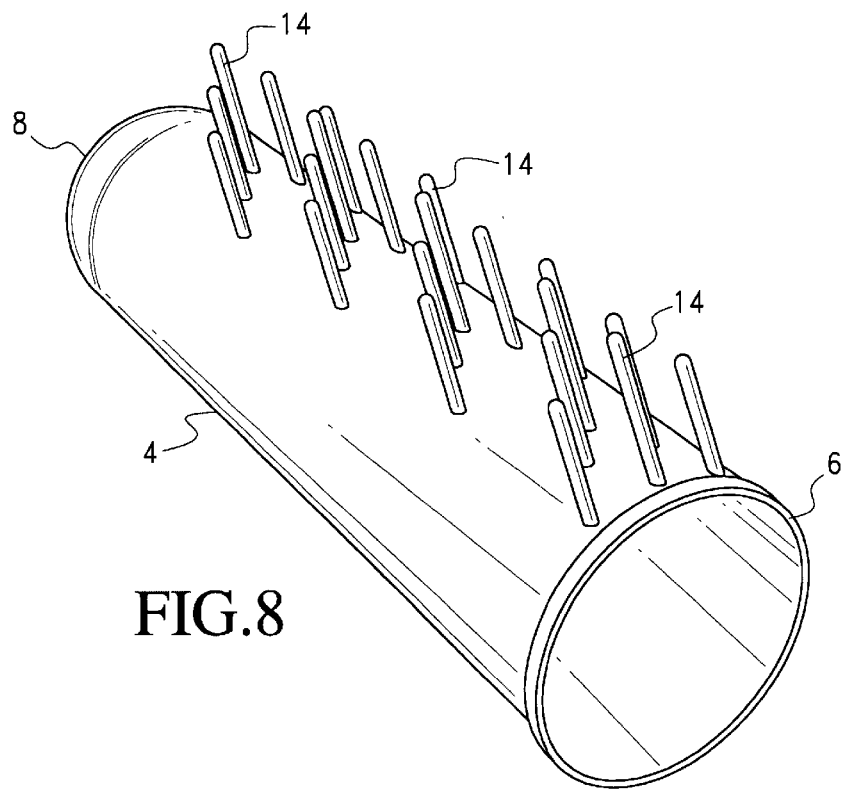
FIG. 8 is a perspective view of the condom shown in FIG. 7.

A fourth embodiment of the invention is shown in FIGS. 7 and 8. As illustrated therein, the condom 2 includes a plurality of lash-like projections 14 wherein the lash-like projections 14 have a length of about 10 mm and in which a forward portion of the body 4 is free of projections over about 25 to 33% of its length.

Figure 9:
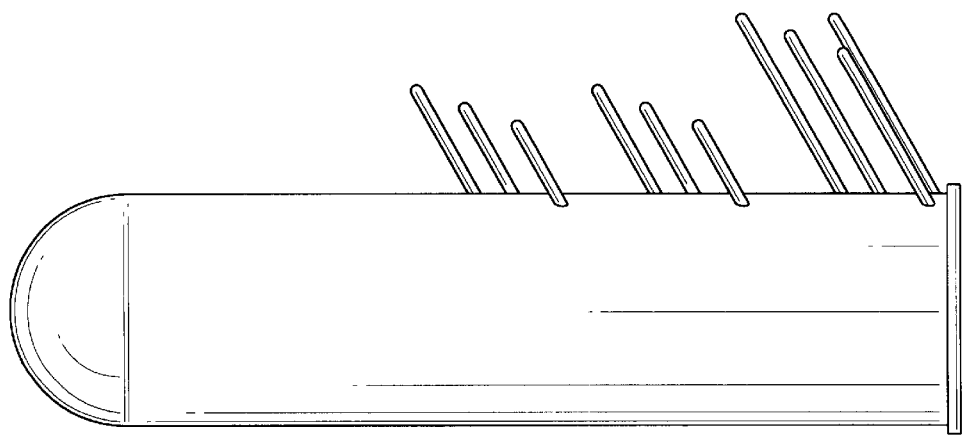
FIG. 9 is a side view of a further embodiment of the invention.
Figure 10:
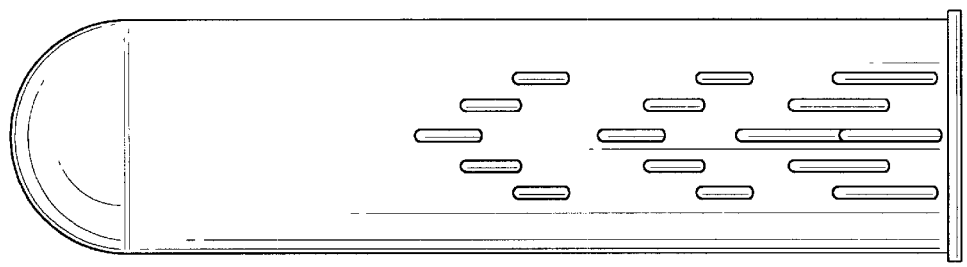
FIG. 10 is a top view of the condom shown in FIG. 9.

As illustrated in FIGS. 9 and 10, the condom 2 includes three arrays of lash-like projections in a V-pattern where the lash-like projections 14 have a relatively short but equal lengths while those at the rear of the tubular body 4 are of a longer length, i.e. about 18 mmm. As illustrated, in this embodiment, the forward portion extends along about 40% of the length of the tubular body and is free of the lash-like projections.

While the invention has been described in accordance with its preferred embodiments, it should be recognized that changes and modifications may be made therein without departing from the scope of the appended claims.

What is claimed is:

1. A condom comprising a flexible tubular body having an open end, a closed end, an outer surface and a smooth inner surface, said tubular body formed of a thin homogeneous elastomeric membrane and having a generally constant diameter from the open end to the closed end to define a longitudinally extending chamber, and said tubular body having a plurality of outwardly extending flexible projections extending outwardly from said outer surface of said tubular body and fixed thereto along one side thereof in which the stiffness of said flexible projections are greater than the stiffness of said flexible tubular body; and in which the thickness of said flexible projections are greater than the thickness of said thin membrane material and wherein said projections have a length to width ratio of between about 5:1 and about 9:1.

2. A condom according to claim 1, in which said flexible projections have a length of about 10 mm to about 18 mm and a thickness of about 2 mm.

3. A condom according to claim 2, wherein said flexible projections are formed of the same material as said tubular body.

4. A condom according to claim 3, in which the minimum longitudinal distance between flexible projections is 12 mm.

5. A condom according to claim 4, wherein said flexible projections are disposed between 4 and 5 longitudinally extending rows of 8 to 9 projections.

6. A condom according to claim 5, wherein said flexible projections are of even length.

7. A condom according to claim 5, wherein said flexible projections near the open end of said tubular body are longer than said flexible projections near to said closed end of said tubular body.

* * * * *